(12) United States Patent
Han et al.

(10) Patent No.: US 6,817,229 B2
(45) Date of Patent: Nov. 16, 2004

(54) ACOUSTIC SENSOR FOR FLUID CHARACTERIZATION

(75) Inventors: Wei Han, Missouri City, TX (US); James R. Birchak, Spring, TX (US); Bruce H. Storm, Jr., Houston, TX (US); Thomas E. Ritter, Katy, TX (US)

(73) Assignee: Halliburton Energy Services, Inc., Houston, TX (US)

( * ) Notice: Subject to any disclaimer, the term of this patent is extended or adjusted under 35 U.S.C. 154(b) by 0 days.

(21) Appl. No.: 10/384,030

(22) Filed: Mar. 7, 2003

(65) Prior Publication Data

US 2003/0150262 A1 Aug. 14, 2003

Related U.S. Application Data

(62) Division of application No. 09/803,850, filed on Mar. 12, 2001, now Pat. No. 6,672,163.
(60) Provisional application No. 60/189,254, filed on Mar. 14, 2000.

(51) Int. Cl.[7] .............................................. G01N 29/00
(52) U.S. Cl. .................................. 73/64.53; 73/152.47
(58) Field of Search ............................ 73/24.01, 24.03, 73/24.06, 861.31, 861.29, 152.58, 865.5, 599, 866.5, 597, 579, 152.18, 152.47, 64.53

(56) References Cited

U.S. PATENT DOCUMENTS

| | | | |
|---|---|---|---|
| 3,906,791 A | * | 9/1975 | Lynnworth ................ 73/861.29 |
| 3,914,984 A | | 10/1975 | Wade .......................... 73/61 R |
| 3,981,176 A | * | 9/1976 | Jacobs ........................ 73/24.01 |
| 4,381,674 A | | 5/1983 | Abts ............................ 73/599 |
| 4,527,420 A | | 7/1985 | Foote .......................... 73/61 R |
| 4,571,693 A | | 2/1986 | Birchak et al. ............. 364/509 |
| 4,580,444 A | | 4/1986 | Abts et al. ...................... 73/61 |
| 4,665,511 A | | 5/1987 | Rodney et al. ............... 367/35 |
| 5,060,506 A | * | 10/1991 | Douglas ..................... 73/24.01 |
| 5,060,514 A | * | 10/1991 | Aylsworth .................. 73/24.01 |
| 5,276,656 A | | 1/1994 | Angehrn et al. .............. 367/86 |
| 5,437,194 A | * | 8/1995 | Lynnworth ............... 73/861.27 |
| 5,597,962 A | * | 1/1997 | Hastings et al. ......... 73/861.29 |
| 5,741,962 A | | 4/1998 | Birchak et al. .......... 73/152.16 |
| 5,924,499 A | | 7/1999 | Birchak et al. ............... 175/40 |
| 6,354,146 B1 | | 3/2002 | Birchak et al. ............ 73/61.79 |

FOREIGN PATENT DOCUMENTS

WO   WO 98/34105   8/1998

OTHER PUBLICATIONS

Zacharias, Jr., E.M. and Ord Jr., R., *Development of Broad Sonic Pipeline Interface Detector*, Oil and Gas Journal, pp. 80–89, Nov. 30, 1981.

(List continued on next page.)

*Primary Examiner*—Robert Raevis
(74) *Attorney, Agent, or Firm*—Michael W. Piper; Rodney B. Carroll; Albert C. Metrailer

(57) ABSTRACT

A method and apparatus for in-situ characterization of downhole fluids in a wellbore using ultrasonic acoustic signals. Measurements of the speed of sound, attenuation of the signal, and acoustic back-scattering are used to provide qualitative and quantitative data as to the composition, nature of solid particulates, compressibility, bubble point, and the oil/water ratio of the fluid. The tool generally comprises three sets of acoustic transducers mounted perpendicular to the direction of the flow. These transducers are capable of operating at different frequencies so that the spectrum of the acoustic signal can be optimized. The apparatus is capable of operating downhole to provide real time information as to conditions in the well.

8 Claims, 3 Drawing Sheets

OTHER PUBLICATIONS

Wang, Z., and Nur, A., *Acoustic Velocities in Petroleum Oils*, J. of Petroleum Technology, pp. 192–200, Feb. 1990.

Verrall, R.E., Heal, G.A. and Dyer, K.L., *Sound Velocity Studies of Pipeline Oils as a Function of Viscosity, Density and Water Content*, Journal of Canadian Petroleum Technology, vol. 33, No. 2, pp. 51–57, 1994.

Smiths, A.R. et al., *In–situ Optical Fluid Analysis as an Aid to Wireline Formation Sampling*, SPE Formation Evaluation, vol. 10, No. 2, 1995, pp. 91–98.

Kino, G., *Acoustic Waves: Devices, Imaging, and Analog Signal Processing*, Prentice–Hall, Inc., NY, 1987.

Allegra, J.R., and Hawley, S.A., *Attenuation of Sound in Suspensions and Emulsions: Theory and Experiments*, J. Acoust. Soc. Am., 51, pp. 1545–1564 (1972).

Bhatia, *Ultrasonic Absorption*, 1967, Oxford University Press, reprinted by Dover Publications, Inc., New York, 1985, pp. 19–26, 49–64, 168–173, 194–263, 371–400.

Han, W., Ph. D. Thesis, *Visco–Thermal Coupling Effects on Acoustic Attenuation in Concentrated Colloidal Dispersions*, University of Maine, 1995.

Urick, R.J., *The Absorption of Sound in Suspensions of Irregular Particles*, J. Acoust. Soc. Am. 20, 283–289.

Hampton, L.D., 1967, *Acoustic Properties of Sediments*, J. Acoust. Soc. Am. 42, 882–890.

Sherman, N.E., 1991, *Ultrasonic Velocity and Attenuation in Aqueous Kaolin Dispersions*, J. Colloid and Interface Sci. 146(2), 405–414.

PCT Search Report for PCT/US01/07978 dated Jun. 22, 2001.

* cited by examiner

ACOUSTIC SENSOR FOR FLUID CHARACTERIZATION

CROSS-REFERENCE TO RELATED APPLICATIONS

This is a divisional of U.S. patent application Ser. No. 09/803,850 filed Mar. 12, 2001, now U.S. Pat. No. 6,672,163 issued on Jan. 6, 2004, which patent claims the benefit of U.S. Provisional Application Ser. No. 60/189,254, filed Mar. 14, 2000, entitled Acoustic Sensor For Fluid Characterization, which is incorporated herein by reference.

FIELD OF THE INVENTION

The present invention relates generally to downhole measurements of fluid properties in a borehole, and more particularly to a tool for characterizing fluids at the bottom of the hole, including fluid flowing into the hole from the formation. Still more particularly, the present invention relates to a tool that uses acoustic measurements, including multi-frequency acoustic measurements, to obtain qualitative and quantitative measurements of the composition and phases of the liquid, its compressibility and its bubble point.

BACKGROUND OF THE INVENTION

During the development and useful life of a hydrocarbon well it is often desirable to evaluate the fluids present in the surrounding formations to determine the quality of hydrocarbons present and the status of the well. Useful information about the formation fluid includes the composition and volume fraction of oil and water, the amount of solids contained in the fluid, compressibility of the fluid, and the pressure at which any entrained gases will bubble out of the fluid (bubble point). This information is helpful in determining the proper procedures to use for drilling and producing the well.

Historically, subterranean reservoir fluids were brought to the surface for analysis. There are many advantages to being able to analyze reservoir fluids while still in the well but downhole sampling and analysis of reservoir fluids presents a number of problems. One problem encountered in data acquisition downhole is the need to obtain a representative sample of reservoir fluid with minimum level of drilling fluid contamination. In the course of drilling, filtrate (drilling-mud based fluid) typically invades the formation in the vicinity of the wellbore. The process of conducting a formation test commonly involves acquiring a sample of reservoir fluid by running a conduit into the wellbore and providing a pressure drop so that fluid will flow into the conduit. The first fluid to reach the tool will comprise mainly the drilling fluid filtrate coming back out of the formation. Over time reservoir fluids displace this filtrate. Since the objective is to sample and analyze the reservoir fluids, rather than the filtrate, it is necessary to wait until the reservoir fluid has substantially displaced the filtrate from the sampling device. Thus, it is desirable to monitor the drilling fluid level in the fluid stream and to determine when an acceptable maximum level of contamination is reached so that a representative fluid sample can be obtained. A maximum level of one hundred parts per million of contaminant is acceptable for all known applications. Even samples with 70% contaminant can sometimes be useful with accurate knowledge of contaminant fraction.

Accordingly, there has been a continuing need to develop a fluid analysis system capable of accurately assessing the quality of the wellbore fluid and measuring the composition of the reservoir fluid. In particular, there has been a need to provide a method and system for measuring level of drilling fluid contamination in fluid sample, and for performing in-situ quantitative fluid analysis to determine gas bubble point, water-oil ratio, fluid composition, and compressibility of the reservoir fluid. Some prior art has disclosed methods of measuring fluid properties downhole but these methods are limited in the amount of information available.

U.S. Pat. No. 3,914,984, issued to Wade, discloses a method of measuring solid and liquid droplets in a liquid using ultrasonic tone-burst transmission in a sample cell. U.S. Pat. No. 4,381,674, issued to Abts, describes a method of detecting and identifying scattering media in an oil recovery system by counting the number of ultrasonic pulses reflected from the scattering media and comparison with the ultrasonic energy attenuation. U.S. Pat. No. 4,527,420, issued to Foote, describes a method and apparatus of using scattered ultrasound to identify solid particles and liquid droplets, specifically for semiconductor and chemical process monitoring applications. International Application Publication No. WO 98/34105, invented by Nyhavn, describes a method and apparatus for inspecting a fluid flow in a hydrocarbon production well using a method of qualitatively analyzing scattering media using acoustic signals scattered or reflected in the fluid flow. U.S. Pat. No. 4,571,693, issued to Birchak et al., describes a device for downhole measurement of multiple parameters such as attenuation, speed of sound, and density of fluids. The device consists of a gap to be filled with the fluids and a void to provide reference echo for attenuation measurement calibration but does not utilize a conduit to enable the flow of fluids through the tool. Other prior art devices have employed optical sensors and utilized a visible and near-infrared absorption spectrometer to identify the type of formation fluid, i.e. to differentiate between oil, drilling mud, water and gas present in the formation fluid. However, the windows of the optical devices may become coated with hydrocarbons (asphaltene, paraffin) that may distort their results. The devices also suffer from small depth of penetration for opaque fluids, which reduces their accuracy.

Despite the teachings of the foregoing references, it is still desired to provide a method for determining drilling fluid contamination and characterizing fluid media in situ. It is further desired to provide a downhole device that can detect and analyze gas bubbles and fine sand particles. Such a device would greatly improve reservoir fluid sampling and testing.

SUMMARY OF THE INVENTION

The present invention relates generally to fluid characterization in downhole reservoir fluid sampling and description applications. More specifically, this disclosure provides a method and apparatus for using acoustic transducers to detect and identify gas bubbles, solid particles, and/or liquid droplets in fluids. In one embodiment, the method comprises transmitting an acoustic signal through the fluid and using the received acoustic signal to determine the speed of sound in the fluid and the attenuation of the signal in the fluid. These measurements, along with a measurement of the density of the fluid can be used to calculate the compressibility of the fluid, fluid composition, solids content, and bubble-point of the fluid.

The present invention measures the fluid speed of sound and acoustic attenuation as a function of frequency and/or pressure. From the speed of sound, the fluid type and presence of mixtures can be determined. From speed of sound data combined with density, the compressibility of the fluid can be determined. Attenuation as a function of pressure is used to determine the bubble point pressure. In turn, these values can be used qualitatively and/or quantitatively to obtain information about the presence and size of solids in the fluid stream, contamination by solids or immiscible liquids, compressibility and the bubble point of the fluid stream.

Capabilities of the present method and apparatus may include, but are not limited to:

providing a qualitative indication of the extent of drilling fluid contamination in formation fluid;

providing a qualitative distinction between gas and liquid, water and oil, and crude oil and drilling mud fluid;

detecting gas vapor and gas bubbles in formation fluids;

providing a way to determine compressibility of the fluid;

providing a quantitative indication of oil/water ratio; and providing a quantitative indication of solid particle size and concentration.

BRIEF DESCRIPTION OF THE DRAWINGS

For a detailed understanding of a preferred embodiment of the invention, reference will be made to the attached Figures, wherein.

Figure 1:
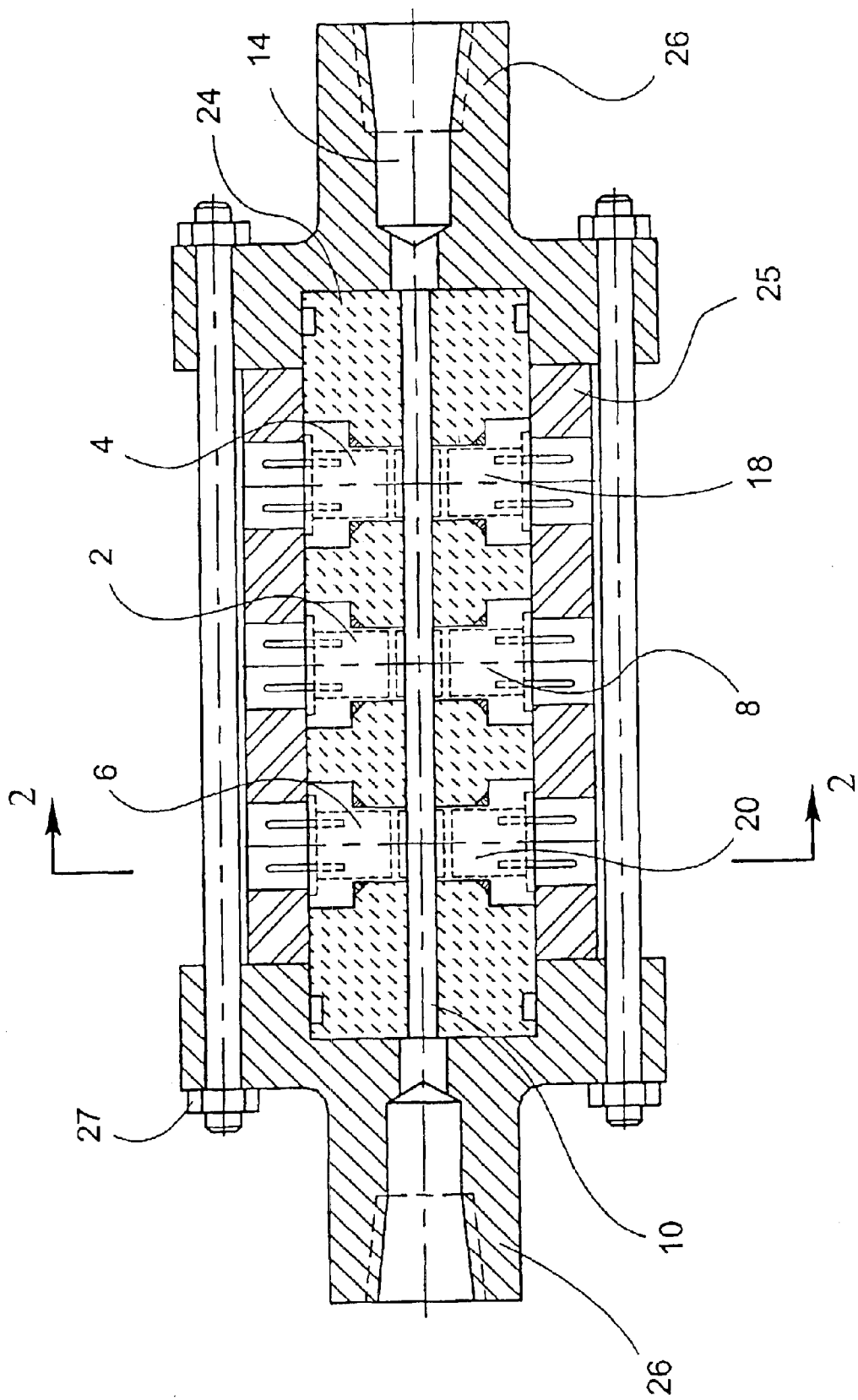
FIG. 1 is a longitudinal cross-section of a tool constructed in accordance with a preferred embodiment of the present invention.

While the invention is susceptible to various modifications and alternative forms, specific embodiments thereof are shown by way of example in the drawings and will herein be described in detail. It should be understood, however, that the drawings and detailed description thereto are not intended to limit the invention to the particular form disclosed, but on the contrary, the intention is to cover all modifications, equivalents and alternatives falling within the spirit and scope of the present invention as defined by the appended claims.

DETAILED DESCRIPTION OF THE PREFERRED EMBODIMENTS

The present invention provides a method and apparatus for analyzing downhole fluids in a wellbore, such as in a formation testing application or in a pipeline, by determining the bubble point of entrained gas, water-oil ratio, fluid composition, and compressibility. Measurements of speed of sound, acoustic back-scattering, density, frequency-dependent attenuation, and pressure-dependent attenuation are collected and used as the basis for a characterization of the wellbore fluids. These measurements are made difficult by the fact that formation fluids generally contain particulates dispersed in a continuous liquid medium. The particulate can be in the form of solid particles (e.g., fine sand), liquid droplets, or gas bubbles.

To assess or characterize the fluid and the dispersed particulate(s), the present system uses at least one ultrasonic acoustic wave that is transmitted into the fluid flow. The transmitted acoustic wave may have finite cycles and may have fixed or variable frequencies. One or more receivers then receive the transmitted signals. The received signal can then be used to determine the speed of sound in the liquid, the acoustic back-scattering caused by impurities in the liquid, and the attenuation, or acoustic energy losses, resulting from traveling through the fluid.

The preferred method of measuring the speed of sound in the liquid is to transmit an acoustic signal over a known distance between a transmitter and a receiver. The speed of sound in the fluid can be measured from the time-of-flight of transmitted signal, as given by $c=D/\Delta t$, where D is the path length (equal in this case to the conduit diameter), and $\Delta t$ is the time-of-flight for the pulse traveling across the fluid. For a fluid consisting of water and oil of known type and temperature, the ratio of water/oil can be determined from speed of sound measurement in the two-phase mixture by comparing the measured speed of sound to known data for speed of sound for the individual components.

Determination of the acoustic energy loss (attenuation) can be used to assess sample contamination in more complex environments. Each transmitting acoustic transducer emits a tone-burst or pulsed signal having a distinct frequency into the fluid. After passing through the fluid sample, the wave is detected by a receiving transducer. The received acoustic signal is controlled by the amount of acoustic energy loss (attenuation) in the fluid sample, as characterized by the attenuation coefficient of the fluid. To evaluate fluid mixtures of solid particles or liquid droplets suspended in a liquid medium, the excess attenuation coefficient is evaluated. The excess attenuation coefficient is the total attenuation in the liquid medium minus losses of the signal that would occur in a liquid without particles or droplets. The extent of acoustic energy loss in the fluid sample results from the combined effect of absorption in the particulate and liquid media, visco-inertial attenuation, thermal attenuation, and acoustic back-scattering loss.

Figure 4:
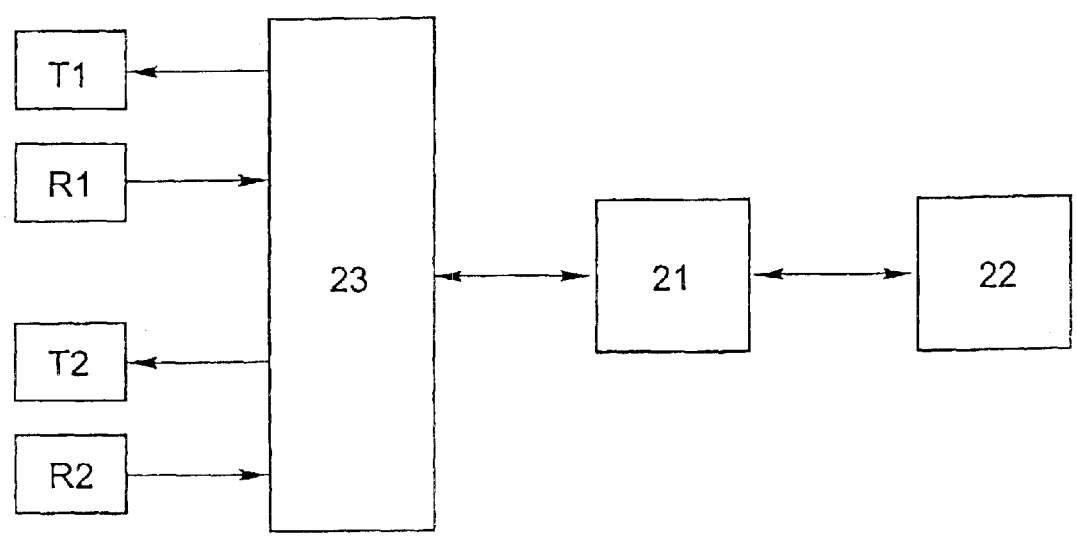
FIG. 4 is a schematic view of the system.

The preferred method of measurement of the compensated attenuation coefficient requires two receivers and two transmitters. Two split element transducers give four elements. In reference to FIG. 4, the transmitters are labeled T1 and T2, and the receivers are R1 and R2, then the attenuation is given by the equation:

$$\alpha = [(V12*V21)/(V11*V22)]^{1/2},$$

where V12 is the signal produced by transmitter T1 in receiver R2, V21 is the signal produced by T2 in R1, V11 is the signal produced by T1 in R1, and V22 is the signal produced by T2 in R2. A microprocessor 21 controls the transmitters and receivers via interface 23 to obtain signal voltage measurements, processes the signal measurements to determine sound attenuation and speed, and transmits the results to the surface via telemetry module 22. Because the measured voltage is proportional to signal strength, the above equation can be used to convert measured voltages into attenuation data.

The preferred fluid analysis method also includes measuring the attenuation coefficient at different frequencies so that the frequency dependence of the attenuation can be determined. In general, the frequency/attenuation relationship can be given as $\alpha = Af^n$, where:

α is the attenuation coefficient;

A is a calibration constant representing the absorption of the liquid, for water A=25 and for castor oil A=10000;

f is the frequency of the transmitted signal;

and n is a power factor that correlates to the solids associated with damping (e.g., for visco-elastic damping n=2 and for visco-inertial n=1). In a pure liquid, attenuation is proportional to frequency squared (n=2). As the amount of solids in the fluid increase, n approaches unity.

From the frequency dependence of the attenuation coefficient, the fluid can be compared to fluids with known attenuation coefficients. The frequency dependence of the attenuation coefficient can therefore form the basis for a qualitative indication of the nature of the fluid stream, and more importantly, the extent of drilling mud fluid contamination in the formation fluid sample.

As an alternative embodiment of this invention, acoustic attenuation as function of frequency or at a constant frequency, can be used to monitor the variation of the solid concentration and thus help determine the relative level of the mud (and mud filtrate) contamination in the formation fluid sampled. For example, water-based drilling mud normally consists of 10-20 wt % of solid particles (i.e., clay, a few microns in size) suspended in a liquid medium (i.e., water). At the start of pumping, the fluid sample would mainly be the mud with known solid concentration. As the portion of the mud (or mud filtrate) decreases and more formation fluid is collected, the solid concentration in the fluid sample would proportionally decrease. Monitoring the solid concentration in the fluid sampled can provide a quantitative measurement of the mud (or mud filtrate) fraction in the fluid sampled. For suspensions of micrometer-sized clay particles suspended in water, previous experimental studies on acoustic attenuation were reported at finite frequencies, 0.1 MHz, 1.0 MHz, 5.0 MHz, and at discrete frequencies from 3-100 MHz. The experimental studies on clay-water dispersions indicate that: 1) at solid weight fraction <22%, the attenuation coefficient is linearly proportional to the frequency up to f=30 MHz; and 2) at constant frequency, the attenuation coefficient is approximately linear, increasing with the solid concentration up to 22 wt %, beyond which point the observed attenuation starts to decrease, due the increased particle-particle interaction. Experimental study of acoustic attenuation in clay-water dispersions indicates that the frequency dependence of the visco-inertial attenuation coefficient is linear to the frequency, that is, $\alpha \propto Bf$, below f<35 MHz. Here B is a factor primarily dependent on the solid concentration and particle size.

The visco-inertial acoustic energy loss results from the relative motion of the suspended particle phase relative to the suspending fluid medium. The loss is dependent on the relative density contrast of the suspended particulate and surrounding fluid medium. Visco-inertial attenuation is the dominant mechanism for acoustic signal loss in suspensions of sub-micron or micron-sized clay or sand particles in water. At high frequency or high concentrations, the visco-inertial attenuation dominates the total attenuation so that the absorption in water may be neglected. At low frequency and low solid concentrations, to get the excess attenuation and evaluate the solid properties more accurately, knowledge of the absorption in the liquid medium is needed. This information can be determined by experimental analysis of known fluids in a controlled environment.

In contrast to visco-inertial losses in suspensions of solids in liquids, for dispersions of oil droplets in water, thermal loss is the dominant loss mechanism. Thermal attenuation is the acoustic energy loss in the form of heat transfer between suspending particle and fluid medium phases. The thermal loss is strongly dependent on the difference in the thermodynamic factor [thermal expansion coefficient/(density× specific heat)] for suspended particulate and fluid phases. The attenuation coefficient for either the visco-inertial or thermal attenuation loss is an approximately linear function of the frequency, that is, $\alpha \propto Bf$.

Scattering loss is a non-absorption process in which an acoustic wave beam is reflected or re-directed from the surface of a particulate, thereby reducing the acoustic transmission. The extent of scattering loss strongly depends on frequency f and size of the scattering particles. More particularly, the scattering loss is approximately related to the scattering particulate size and frequency as $\alpha \propto f^4 a^3$ where a is particle diameter, for particulates smaller than the signal wavelength.

For particles comparable to or larger than the wavelength, specular reflection occurs. Specular loss is relatively independent of frequency. Fine particle size originated from the drilling fluid or from the formation may also be measured using the attenuation spectrum. For an emulsion containing a small amount of one liquid as highly dispersed droplets, the attenuation vs. fourth power of frequency may be most suitable.

The preferred embodiment of the present invention also provides a method for determining the compressibility of the fluid using the measured speed of sound in fluid stream and density. Compressibility helps to determine the relative concentrations of solids, liquids and gases in multi-phase systems. Density can be measured using a standard densitometer (not shown). For a fluid medium with a known density, the compressibility of the fluid $\beta$ is determined by $\beta=1/(c^2\rho)$.

In turn, measurement of the sound speed and calculation of the fluid compressibility, in conjunction with attenuation measurement discussed above, can give a qualitative indication of the presence of a gas phase in the fluid stream. Gas volume fraction relates linearly to incremental compressibility.

The preferred embodiment also seeks to determine the pressure at which gas entrained in the liquid will begin to bubble out, known as the bubble point. Monitoring for gas bubbles and for the bubble-point can also help optimize pumping control of sample fluid and representative sample collection. Gas evolution from the formation fluid must be avoided during sampling, which requires that the sampling pressure be above the bubble-point pressure of the fluid. When the fluid is determined to consist primarily of reservoir fluid, or equilibrium conditions in the test tool have been achieved, the bubble point of the reservoir fluid can be determined. This can be accomplished by monitoring the pressure and testing for the evolution of gas bubbles with acoustic attenuation and/or scattering measurements as the pressure of the system is lowered from an initial pressure above the bubble point. As the pressure reaches the bubble point, free gas vapor appears and the acoustic attenuation and scattering increase abruptly. By detecting the formation of gas bubbles and hence determining the bubble point pressure, the pumping operation can be monitored and adjusted to maintain the sampling pressure above the bubble point pressure. Thus sampling conditions at which no gas evolves in the formation fluid can be determined, allowing representative formation fluid sample to be collected.

If the sampling pressure is above bubble-point pressure, as is required by the requirement of collecting representative formation fluid, no gas phase exists and the mixture will comprise one or more liquid phases in addition to a solids phase. If the solids concentration is very small, then the fluid essentially becomes a water and oil two-phase mixture. As discussed above, for water and oil of known type at temperature T, the ratio of water/oil can be determined from speed of sound measurement in the two-phase mixture by comparing the measured speed of sound to known data for a speed of sound for the individual components.

The disclosed methods for measuring the speed of sound of the fluid and the acoustic attenuation coefficient as function of frequency allow for characterization of the particulate and the fluid streams. In particular, the method disclosed makes it possible to distinguish between gas and liquid, oil and water, and crude oil and drilling mud filtrate. For example, when a fluid stream is introduced into a formation-testing tool, the character of the fluid entering the tool changes as a function of time: from drilling mud to drilling fluid filtrate, and then to reservoir fluid as the dominant component. The solids content of the flow stream also changes, decreasing over time. The compressibility of the system increases as more gas is present in the reservoir fluid. Each of these features affects the transmission, and speed of incident acoustic radiation, providing signatures whereby changes in the fluid may be monitored.

In addition, using the measured fluid density and the measured speed of sound, the acoustic impedance can be calculated as (z=ρc) as the product of the density (ρ) and the speed of sound (c). Attenuation measurements are preferably compensated for transmission losses due to changing impedance mismatch between transducer and fluid. The transmission loss associated with the impedance mismatch can be calculated once the fluid acoustic impedance is known and used to calculate a true attenuation that is compensated for transmission loss associated with the impedance mismatch. An alternate method of measuring acoustic impedance is using a medium of known acoustic impedance between the piezoelectric element and the fluid. The reflection amplitude from the medium/fluid interface can be used knowing the known acoustic impedance of the medium to calculate acoustic impedance of the fluid. The medium is called a delay line. The product of the acoustic impedance measured with a delay line and the speed of sound equals the inverse of the compressibility. Hence, compressibility can be derived without a separate density measurement if a delay line is used.

The present method and system are particularly advantageous when the formation is one that produces a gas condensate. Specifically, the attenuation measurements described above can be performed over a range of pressures. This present technique provides a sensitive way to determine the presence of gas in the sample, because as the attenuation is measured as a function of pressure, it will rise sharply when the dissolved gas begins to form bubbles. In some instances, it may be possible to measure the speed of sound of the gas, using the lowest signal frequencies of the tool. If it can be obtained, this speed of sound data can be used to help identify the molecular weight of the gas.

Figure 3:
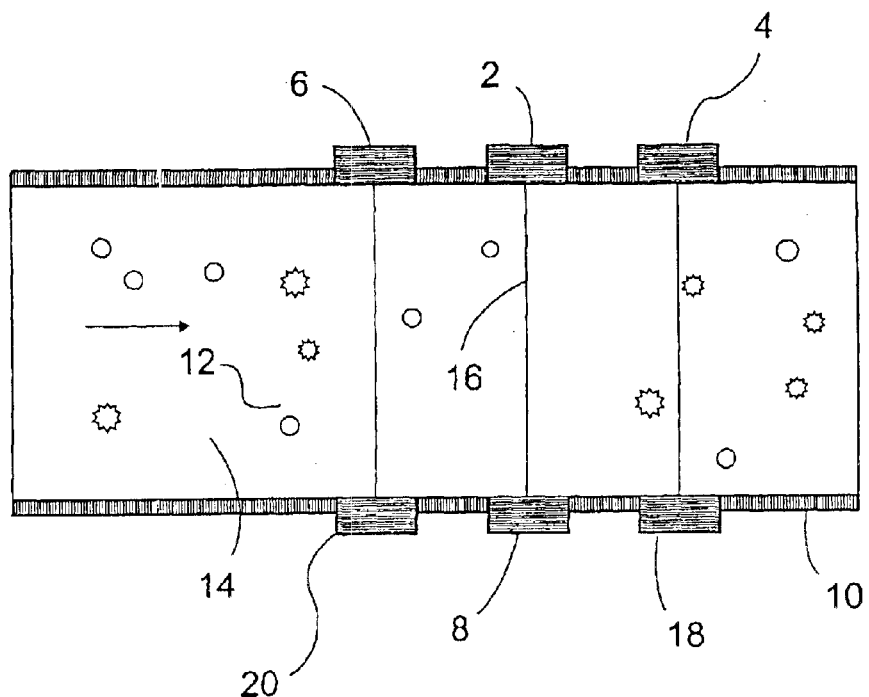
FIG. 3 is a schematic view of a tool constructed in accordance with a preferred embodiment.

As shown in FIG. 1, a preferred embodiment of a tool adapted to carry out the measurements required by the present method comprises three transmitting transducers 2, 4, 6 and three receiving transducers 8, 18, and 20 arranged at various positions along a conduit 10. Receiving transducer 8 is mounted opposite to the transducer 2 to measure the signals from the transducer 2 transmitted through the fluid. Transducers 18 and 20 receive signals transmitted from transmitters 4 and 6 respectively. The flowing fluid in conduit 10 contains particles 12 and a liquid medium 14 (FIG. 3). Transmitter 2 emits several cycles of tone-burst signals having a acoustic frequency f at a repetitive time interval T. Under turbulent flow or well-mixed conditions, the fluid in the volume of interrogation can be considered representative of the bulk fluids in the conduit.

A fluid characterization device generally in accordance with FIG. 1 is configured as follows. A preferred fluid path 10 is at least five wavelengths (wavelength=speed of sound/frequency). The speed of sound for gas is about 0.3 mm/μs, while the speed of sound for liquids varies from about 0.8 mm/μs to 2 mm/μs. The preferred operating frequency varies from 2 MHz to 20 MHz. As a result, the fluid path 10 is preferably at least 0.5 mm to enable any meaningful measurement in fastest fluids. A preferred fluid path is approximately 3.2 mm. This value is good for all conditions except possibly below 3 MHz, where fast liquids may have resolution problems.

In order to ensure that the received signal contains only the desired signal and does not contain extraneous energy, the path from the transmitting transducer to the receiving transducer through the housing should be slower than the fluid path. Hence, a preferred housing 24 is designed so that the estimated path through housing 24 is expected to be longer than the fluid path for liquids. For gas, however, the fluid path may be slower than the housing path and the signals may be weak. A preferred housing material is a tetrafluoroethylene polymer, such as TEFLON®, manufactured by DuPont. The speed of sound in the preferred polymer is about 1.4 mm/μs, which is slower than the speed of sound in water. In addition, the shape of the housing gives a housing path that is longer than the fluid path length.

The transducers are held in the housing 24 by a clamshell housing 25. Either end of the clamshell housing 25 is contained by a flange 26 that allows for attachment to a conduit for running into a wellbore. A series of bolts 27 span between the two flanges 26 and hold the apparatus together.

According to the preferred embodiment, a first opposed pair of transducers, for example 20, 6, with one serving as transmitter and the other as receiver, is used for attenuation and speed of sound measurement at a low frequency. The second pair of transducers 2, 8 and the third pair 4, 18 measure the speed of sound and attenuation at intermediate and high frequencies. These three sets of transducers are preferably broad band in frequency and have different center resonance frequencies. One major advantage of having a wide frequency band is that the attenuation coefficient can be measured over a wide range of frequencies, and thus provide more distinct characterization of the fluid properties. Depending on the fluid systems and attenuation properties, it may be also necessary to use more pairs than the disclosed three-pair transducers, so as to provide a sufficiently wide frequency band. Lower frequencies than 2 MHz may be useful for high mud weight. Higher frequencies than 15 MHz may be needed to distinguish among single-phase liquids.

Alternatively, in another embodiment, the frequency range for one or more of the transducers can be extended by using its third harmonic frequency response. For example, a single piezoelectric transducer element can be excited at its fundamental and third harmonic. By using electronic filtering of the transmitter and received signals, the element can be operated at either frequency, thereby helping to determine the frequency dependence from a fixed configuration comprising a limited number of transducers. The ratio of the two measurements will be relatively stable because transducer variations with environmental conditions have little effect on the sensitivity of the ratio. By operating each transducer at multiple frequencies, fewer transducers are needed to generate the frequency dependence data. For example, a system might include a 1 MHz transducer operated at 1 MHz and 3 MHz and a 9 MHz transducer operated at 9 MHz and 27 MHz.

Speed of sound in the fluid can be calculated by measuring the time of flight of the pulse over the known distance between transmitter 2 and receiver 8. Once the speed of sound is determined, scattered signals measured by transducers 4 and 6 can be identified and gated for analysis. The receiver 8 is also used to determine the attenuation coefficient of the fluid, preferably at multiple frequencies (including third harmonics), by measuring the decay of multiple reflected signals, or comparing the transmitted signals to those of a fluid with known attenuation coefficient.

The tool illustrated in FIG. 1 would be attached to a conduit and lowered into a wellbore. A pump at the surface would be activated drawing liquid from the wellbore up through the tool. Monitoring of data acquired by the tool and method discussed above would show the gradual change of the fluid in the tool from primarily drilling mud to primarily formation fluids. This change would likely be evidenced by a decrease of solids and an increase of hydrocarbons in the form of oil droplets or entrained gas. Therefore, the present method and apparatus allow a meaningful qualitative and quantitative assessment, of the formation fluid, to be made downhole. Hence, the present invention removes the delay normally associated with transit of the fluid sample to the surface and thus makes operations more efficient. Also, by providing essentially real-time fluid information, it is possible to react much more quickly to changes in the formation fluid and therefore enhance safe operation of the well.

In addition to the foregoing, the following U.S. Patents are incorporated herein in their entireties: U.S. Pat. Nos. 5,924,499, 5,763,773, and 5,841,734.

Figure 2:
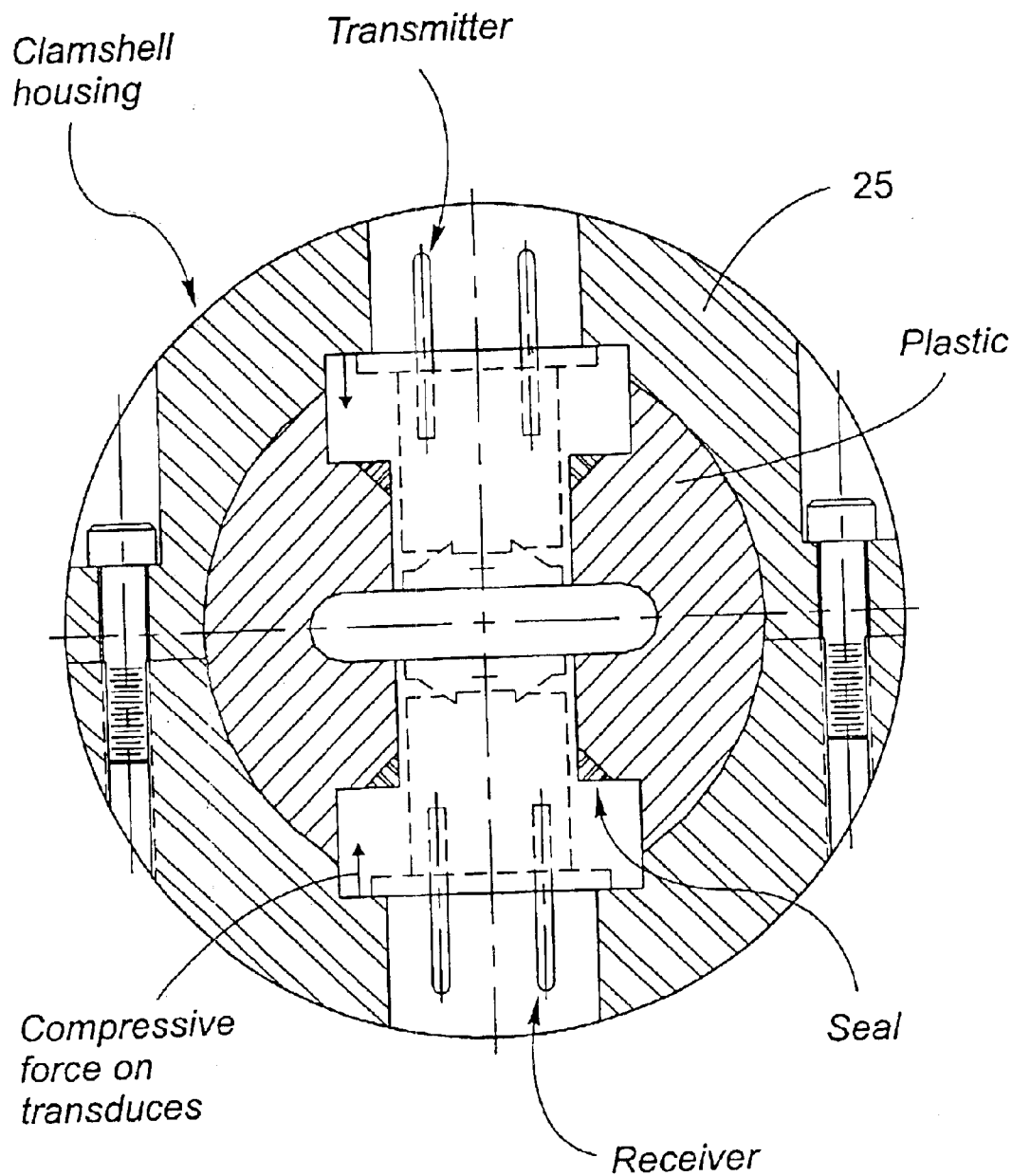
FIG. 2 is a cross-sectional view taken along lines 2-2 of FIG. 1.

While a preferred embodiment has been shown and described, it will be understood that various modifications can be made thereto without departing from the scope of the invention. For example, the measurements and calculations described herein can be made alone or in combination, the number, frequency and arrangement of the transducers can be varied, and the number of measurements and the number of frequencies used can be varied. Furthermore, while a preferred embodiment uses a clamshell housing as shown in FIGS. 1 and 2, so as to achieve a compressive force on the transducers and maintain a fluid seal, other housings and configurations can likewise be used.

What is claimed is:

1. An apparatus comprising
    a tool body comprising end connections for attachment to a conduit and allowing axial flow of fluids;
    a housing disposed within said tool body and having a fluid path; and
    at least two pairs of acoustic transducers located in said housing, each pair having a transmitter element and a receiver element;
    wherein said fluid path is at least 0.5 mm wide between said transmitter element and said receiver element of each pair of acoustic transducers.

2. The apparatus of claim 1 wherein said fluid path is at between 3.0 mm and 3.5 mm wide between said transmitter element and said receiver element.

3. The apparatus of claim 1 wherein each of said pair of acoustic transducers operates at a different fundamental harmonic frequency.

4. The apparatus of claim 1 wherein said acoustic transducers operate between 2 MHz and 20 MHz.

5. The apparatus of claim 1 wherein said housing is constructed of a tetrafluoroethylene polymer.

6. An apparatus comprising
    a tool body with end connections for attachment to a conduit and allowing axial flow of fluids;
    a housing disposed within said tool body and having a fluid path;
    two pairs of acoustic transducers located in said housing, the first pair being low frequency acoustic transducer and the second pair being high frequency acoustic transducers; and
    a third pair of acoustic transducers located in said housing operating at a frequency between said first pair and said second pair.

7. An apparatus comprising
    a tool body with end connections for attachment to a conduit and allowing axial flow of fluids;
    a housing disposed within said tool body and having a fluid path; and
    two pairs of acoustic transducers located in said housing, the first pair being low frequency acoustic transducers and the second pair being high frequency acoustic transducers; wherein said low frequency transducer has a fundamental harmonic frequency below 20 MHz.

8. The apparatus of claim 7 wherein said high frequency transducer has a fundamental harmonic frequency below 20 MHz.

* * * * *

UNITED STATES PATENT AND TRADEMARK OFFICE
CERTIFICATE OF CORRECTION

PATENT NO. : 6,817,229 B2
DATED : November 16, 2004
INVENTOR(S) : Han et al.

It is certified that error appears in the above-identified patent and that said Letters Patent is hereby corrected as shown below:

<u>Column 10,</u>
Line 25, replace "transducer" by -- transducers --
Line 41, replace "below 20" by -- above 2 --

Signed and Sealed this

Nineteenth Day of April, 2005

JON W. DUDAS
*Director of the United States Patent and Trademark Office*